(12) United States Patent
Warkentine et al.

(10) Patent No.: US 9,044,345 B2
(45) Date of Patent: Jun. 2, 2015

(54) NAVIGATED PLACEMENT OF PELVIC IMPLANT BASED ON COMBINED ANTEVERSION BY APPLYING RANAWAT'S SIGN OR VIA ARITHMETIC FORMULA

(75) Inventors: Blaine Warkentine, Royersford, PA (US); Heiko Mueller, Munich (DE)

(73) Assignee: Brainlab AG, Feldkirchen (DE)

( * ) Notice: Subject to any disclaimer, the term of this patent is extended or adjusted under 35 U.S.C. 154(b) by 1556 days.

(21) Appl. No.: 11/752,105

(22) Filed: May 22, 2007

(65) Prior Publication Data
US 2008/0294265 A1 Nov. 27, 2008

(51) Int. Cl.
| A61F 2/32 | (2006.01) |
| A61B 17/56 | (2006.01) |
| A61F 2/46 | (2006.01) |
| A61B 17/17 | (2006.01) |
| A61B 19/00 | (2006.01) |
| A61B 17/00 | (2006.01) |
| A61F 2/34 | (2006.01) |
| A61F 2/36 | (2006.01) |
| A61F 2/30 | (2006.01) |

(52) U.S. Cl.
CPC ........... *A61F 2/4657* (2013.01); *A61B 17/1746* (2013.01); *A61B 17/175* (2013.01); *A61B 19/50* (2013.01); *A61B 19/52* (2013.01); *A61B 19/5244* (2013.01); *A61B 19/56* (2013.01); *A61B 2017/00017* (2013.01); *A61B 2017/00199* (2013.01); *A61B 2017/00716* (2013.01); *A61B 2019/467* (2013.01); *A61B 2019/501* (2013.01); *A61B 2019/508* (2013.01); *A61B 2019/5255* (2013.01); *A61B 2019/5483* (2013.01); *A61B 2019/566* (2013.01); *A61F 2/32* (2013.01); *A61F 2/34* (2013.01); *A61F 2/36* (2013.01); *A61F 2/4607* (2013.01); *A61F 2/4609* (2013.01); *A61F 2002/30948* (2013.01); *A61F 2002/4632* (2013.01); *A61F 2002/4633* (2013.01); *A61F 2002/4668* (2013.01)

(58) Field of Classification Search
USPC .......................................... 623/22.12; 606/91
See application file for complete search history.

(56) References Cited

U.S. PATENT DOCUMENTS

| 5,290,315 | A | * | 3/1994 | DeCarlo, Jr. .................... 606/89 |
| 6,205,411 | B1 | | 3/2001 | DiGioia, III et al. |
| 2003/0153829 | A1 | * | 8/2003 | Sarin et al. .................... 600/426 |
| 2004/0147926 | A1 | | 7/2004 | Iversen |
| 2006/0095047 | A1 | | 5/2006 | de la Barrera |

FOREIGN PATENT DOCUMENTS

| WO | 04/001569 | 12/2003 |
| WO | 2006/079211 | 8/2006 |

OTHER PUBLICATIONS

International Search Report for European Application No. 08150634 7 dated Sep. 2, 2008.

(Continued)

*Primary Examiner* — Bruce E Snow
*Assistant Examiner* — Melissa Hoban
(74) *Attorney, Agent, or Firm* — Tucker Ellis LLP (57) ABSTRACT

A method for placing a pelvic implant including a cup and a femoral stem includes planning at least one of a location of the cup within a pelvis and a location of the stem within a femur such that a combined anteversion between a predetermined cup component and a predetermined femoral stem component satisfies a predetermined combined anteversion.

14 Claims, 5 Drawing Sheets

(56) References Cited

OTHER PUBLICATIONS

D'Lima et al., "The Effect of the Orientation of the Acetabular and Femoral Components on the Range of Motion of the Hip at Different Head-Neck Ratios", The Journal of Bone and Joint Surgery, Jul. 2006, pp. 315-321.

Widmer et al., "Compliant positioning of total hip components for optimal range of motion", Journal of Orthopaedic Research, 2004, pp. 815-821.

Fumihiro Yoshimine, "The safe-zones for combined cup and neck anteversions that fulfill the essential range of motion and their optimum combination in total hip replacements", Journal of Biomechanics, 2006, pp. 1315-1323.

* cited by examiner

NAVIGATED PLACEMENT OF PELVIC IMPLANT BASED ON COMBINED ANTEVERSION BY APPLYING RANAWAT'S SIGN OR VIA ARITHMETIC FORMULA

FIELD OF THE INVENTION

The present invention relates generally to hip implants and, more particularly, to a method and device for planning and performing the placement of a cup and femoral stem in hip implant surgery.

BACKGROUND OF THE INVENTION

An artificial hip joint has two main components; a prosthesis stem (also referred to as a femoral stem) and a cup. One end of the femoral stem is provided either with a spherical ball head or a prosthesis neck on which can be placed a ball head, where the ball head is designed for a close, sliding fit in a spherical recess of the cup. Together, the femoral stem with the ball head and the cup will act as a ball joint to replace the natural ball joint of the hip. The other end of the femoral stem comprises an elongated part designed to be attached to the hollow femoral canal in the patient's femur.

The cup is designed to be attached to a cavity in the patient's pelvis. A hemispherical shaped, recess in the cup is linked with an exterior surface designed to be attached to the pelvis via a side face. The exterior surface may have various shapes, all according to the method of attachment to the pelvis and other choices made by the supplier. Several of the cups that are in use are shaped as an approximate hemisphere, where the outer hemispherical surface is designed to be cemented to the pelvis. The side face that connects the recess and the exterior surface may be flat or possibly inwardly sloping towards the recess, which is preferably approximately centered in the side face. While the femoral stem and the cup may be fixed to the femur and the pelvis respectively using cement, a cement-free force fit also is possible.

When replacing a worn out hip with a prosthesis, the head of the femur is replaced. This is done by cutting the neck of the femur and hollowing out the top of the femoral canal in order to make room for the elongated femoral stem that is either cemented into the hole or force fitted. Further, the cavity on the pelvis is milled out to receive the cup, which is then fixed either by means of cement or a force fit. If the ball head is detachable, it is placed on the femoral stem before the ball head is placed in the cup, the joint is assembled by lifting the patient's leg up to a natural position and inserting the ball head in the recess in the cup, whereupon the incision is closed.

Conventional methods of positioning the implant (i.e., the cup and the femoral stem) focus on the range of motion of the artificial hip joint to find the optimal cup and stem position. More specifically, the surgeon, without navigation, will place the stem and cup and then perform a trial. At some point before the closure, the surgeon, to assess stability, will do impingement testing, shuck testing and will hold the hip in neutral flexion extension and ab/adduction, while internally rotating the hip a subjective 30-40 degrees. With the leg internally rotated, a well positioned implant should have the calcar of the trial implant entering the cup central to the apex of the cup. If the cup and stem combination is well placed in relation to the anteversion for both components, then the implant has the greatest chance of eliminating dislocation, and with eventual greater range of motion.

Modern navigation techniques allow precise positioning of the cup relative to the anterior pelvic plane (APP). The APP describes a safe zone for the relationship between the cup and the prosthesis stem with respect to the patient's hip geometry. However, such methods do not take into account the personal differences in hip mechanics and stability. Further, variations in pelvic tilt, for example, can affect the resulting spatial orientation of the cup.

For example, studies of pelvic tilt have shown that the average pelvic tilt at rest is about −4 degrees in the lying position and about −8 degrees in the standing position. Further, the pelvic tilt range between individuals, for example, may vary between −27 degrees and +3 degrees.

Pelvic reclination of 1 degree will lead to functional anteversion of the cup by approximately 0.7 degrees. Thus, navigation systems that reference the APP can be inaccurate due to pelvic tilt.

SUMMARY OF THE INVENTION

A goal of total hip arthoplasty (THA) is to perform reconstruction of the hip joint such that the patient will have a pain-free range of motion without impingement.

The present invention can be used to position a cup and femoral stem in hip replacement surgery. More specifically, a placement plan can be developed prior to actual trial of the components, wherein the planned placement minimizes the likelihood of impingement of the joint. With the assistance of a navigation system or the like, the cup and femoral stem can be precisely navigated into position according to the plan. This can provide the patient with a long lasting artificial hip joint that has a wide range of motion and a low likelihood of impingement.

Instead of placing the cup and femoral stem based on an arbitrary plane of the pelvis, the planned placement of the cup and stem can be based on achieving stability through combined anteversion. The theory of combined anteversion proposes a relationship between the cup and stem components that minimizes impingement of the joint. According to combined anteversion, an anteversion angle of a cup component can be made dependent on an anteversion angle of a stem component (or vice versa). Further, this can be done neutral with respect to the stem component (e.g., along the femoral neck axis) by adding a certain anteversion angle to the cup component (or the stem component). This added anteversion angle may be derived using Ranawat's sign or by applying an arithmetic formula as described by Yoshimine or others including Widmer and Jolles. Then, with the assistance of a medical navigation system, for example, the cup and stem can be placed according to the plan.

According to one aspect of the invention, there is provided a method for placing a pelvic implant including a cup and a femoral stem, comprising planning at least one of a location of the cup within a pelvis and a location of the stem within a femur such that a combined anteversion between a predetermined cup component and a predetermined femoral stem component satisfies a predetermined combined anteversion.

According to one aspect of the invention, the method further includes navigating the cup and/or femoral stem into position based on the plan.

According to one aspect of the invention, the cup component is an axis central to an apex of the cup, and the femoral stem component is an axis on a longitudinal centerline of a neck of the femoral stem.

According to one aspect of the invention, the method further includes registering the pelvis and femur in a medical workspace; obtaining from the registered pelvis and femur a transformation matrix for transferring information regarding the femur to a pelvic coordinate system; using the transformation matrix to transfer a neck axis to the pelvic coordinate system; aligning the neck axis through a center of the an acetabulum of the pelvis; and placing the cup component along the neck axis.

According to one aspect of the invention, registering includes: placing the leg in a neutral orientation; determining a trajectory of the femur while the leg is in the neutral position; and storing the trajectory as a zero point for flexion, extension internal rotation, external rotation, and/or ab/adduction of the femur.

According to one aspect of the invention, planning includes using Ranawat's sign to determine an anteversion to be added to a cup axis of the cup and/or a neck axis of the femoral stem so as to achieve the predetermined combined anteversion.

According to one aspect of the invention, planning includes using the formula $\beta_{anat}+0.77*b+\alpha=84.3$ to determine an anteversion of the cup component and/or the femoral stem component.

According to one aspect of the invention, planning includes determining a geometry of the femoral stem after the cup has been placed in the pelvis.

According to one aspect of the invention, planning includes determining a location of the cup after placing the femoral stem in the femur.

According to one aspect of the invention, the method further includes adjusting geometric features of the stem so as to achieve the predetermined combined anteversion.

According to one aspect of the invention, planning at least one of the location of the cup within the pelvis and the location of the stem within the femur includes identifying a cup axis of the cup and a neck axis of the femoral stem, and placing an anteversion of the cup axis dependent on an anteversion of the neck axis, or placing an anteversion of the neck axis dependent on an anteversion of the cup axis.

According to one aspect of the invention, the method further includes placing the cup component neutral with respect to the femoral stem component.

According to one aspect of the invention, placing the cup component neutral includes adding anteversion to the cup component.

According to one aspect of the invention, the predetermined combined anteversion is between 30 degrees and 45 degrees.

According to one aspect of the invention, planning includes: predicting a location of an impingement of the pelvic implant; and selecting a cup placement relative to the predicted impingement locations so as to minimize the occurrence of the impingement.

According to one aspect of the invention, there is provided a computer program embodied on a computer readable medium for placing a pelvic implant including a cup and a femoral stem, comprising code that plans at least one of a location of the cup within a pelvis and a location of the stem within a femur such that a combined anteversion between a predetermined cup component and a predetermined femoral stem component satisfies a predetermined combined anteversion.

According to one aspect of the invention, there is provided a device for placing a pelvic implant including a cup and a femoral stem, comprising: a tracking device operative to localize objects in three-dimensional space; a computational unit operatively coupled to the tracking device, said computation unit including logic operative to plan at least one of a location of the cup within a pelvis and a location of the stem within a femur such that a combined anteversion between a predetermined cup component and a predetermined femoral stem component satisfies a predetermined combined anteversion.

According to one aspect of the invention, the device includes logic operative to navigate the cup and/or femoral stem placement to achieve the target combined anteversion.

According to one aspect of the invention, the device includes a display device operative to provide navigation information during an implant procedure.

According to one aspect of the invention, the computational unit is further operative to register the pelvis and femur in a medical workspace; obtain from the registered pelvis and femur a transformation matrix for transferring information regarding the femur to a pelvic coordinate system; use the transformation matrix to transfer a neck axis to the pelvic coordinate system; direct the alignment of the neck axis through a center of the an acetabulum of the pelvis; direct the placement of the cup component along the neck axis; and determine an anteversion to be added to the cup component and/or the stem component so as to achieve the target combined anteversion.

According to one aspect of the invention, the computational unit is operative to use Ranawat's sign to determine an anteversion to be added to a cup axis of the cup and/or a neck axis of the femoral stem so as to achieve the target combined anteversion.

According to one aspect of the invention, the device includes, the computational unit is operative to use the formula $\beta_{anat}+0.77*b+\alpha=84.3$ to determine an anteversion of the cup component and/or the femoral stem component.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed.

BRIEF DESCRIPTION OF THE DRAWINGS

The forgoing and other features of the invention are hereinafter discussed with reference to the drawing.

DETAILED DESCRIPTION

Artificial hips generally include two components; a cup that is attached to the pelvis, and a stem that is attached to the femur. The femoral stem may include a head portion coupled to an elongated stem portion via a neck portion. Conventionally, hip implants are performed by first positioning the cup, and then placing the stem in relation to the cup. A problem with this approach, however, is that the cup is free in its rotational alignments, while the stem is restricted in its rotational alignments. Thus, if there are alignment or positioning errors with the cup once it has been attached to the pelvis, there my not be sufficient positioning freedom in the stem to compensate for the mis-alignment. This can affect the overall geometry of the implanted hip joint, which can lead to impingement and possible dislocation.

The present invention enables placement of a hip implant within a patient to be planned (prior to trial fittings) such that the likelihood of impingement in the hip joint is minimized. As used herein, a planned placement includes establishing a geometrical relationship between the cup and femoral stem (or components thereof) prior to actual trial fittings.

Placement of the hip implant, which may include a cup that is inserted into the pelvis and a femoral stem that is inserted into the femur, is planned using the principle of combined anteversion in combination with medical navigation. Further, placement of the cup may be based on a verified position of the stem (i.e., the stem may be used as an initial parameter for cup placement). In other words, a "stem first" approach may be implemented.

Once the placement of the cup and stem is planned, a prediction can be made where primary impingement of the joint may occur. This data can be filtered to maximize cup placement relative to known primary impingements of the implants.

Figure 1:
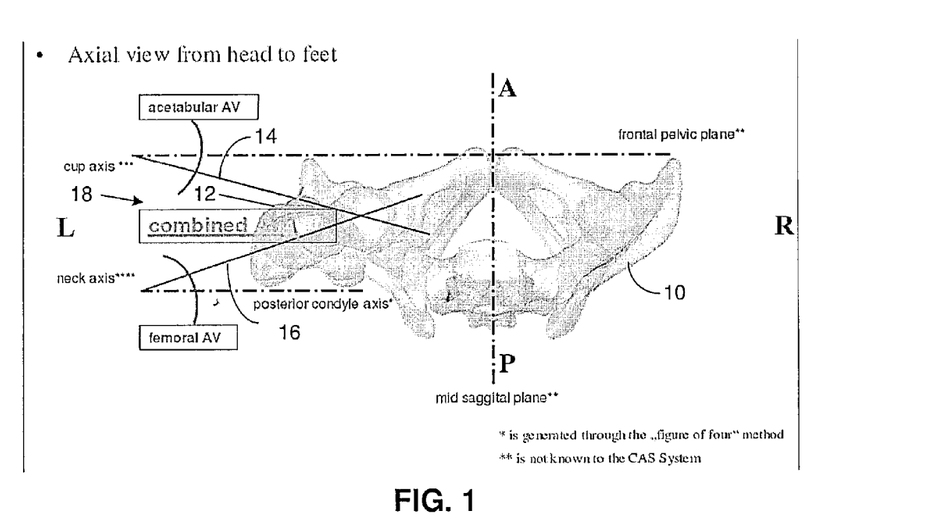
FIG. 1 is a schematic diagram illustrating the principle of combined anteversion.

With reference to FIG. 1, there is shown an axial view of a pelvis 10 and femur 12 from the head to the feet. When applying the principle of combined anteversion, an anteversion angle of a cup component may be dependent on an anteversion angle of a stem component (or vice versa) so as to achieve a desired combined anteversion. The cup component may be an axis entering the cup central to an apex of the cup, while the stem component may be a longitudinal centerline of the femoral neck, for example. Preferably, the combined anteversion 18 (i.e., the combination of the cup anteversion and the neck anteversion) is between about 30 degrees and 45 degrees, although other angular relationships are possible.

In planning the position of the cup and femoral stem, a cup axis 14 (e.g., the cup component or axis entering the cup central to the apex of the cup), for example, can be made dependent on a neck axis 16 (e.g., the stem component or the longitudinal centerline of the femoral neck) such that the combined anteversion is neutral (i.e., along the neck axis of the femur) by adding a certain anteversion angle. The added anteversion angle, which achieves the desired combined anteversion, may be determined, for example, based on Ranawat's sign.

As is well known by those having ordinary skill in the art, Ranawat's sign refers to a method of checking alignment of a hip implant based on internal rotation of the hip components. More specifically, a trial implantation of the components (i.e., the stem and cup) may be performed, and then from a neutral position, the patient's leg may be rotated 45 degrees such that the neck or trunion projects toward a middle region of the cup. If the neck projects substantially to the middle region of the cup, then this indicates that the stem and cup are properly matched. If the neck does not substantially project toward the middle region of the cup, then the alignment is improper. To overcome the improper alignment, the implants may be repositioned and/or different implants may be utilized.

In the present case, however, instead of applying Ranawat's sign after trial of the implant, it can be virtually applied to the planned placement of the cup and femoral stem prior to trial fittings of the implant. With computer assistance, various geometrical relationships between the cup and stem, as well as different cups and stems, can be analyzed so as to determine a plan that best satisfies Ranawat's sign. Once a plan is accepted, it can be carried out with the assistance of computer navigation so as to precisely position the cup and stem according to the plan.

By utilizing Ranawat's sign in the planning stage in combination with medical navigation in the implementation stage, the precise anteversion angle to be added to the cup anteversion and/or neck anteversion so as to achieve the target combined anteversion can be determined and set. This can minimize the likelihood of impingement of the hip joint.

Further, the results of a trial and/or final implant also can be verified using a medical navigation system. For example, a cup and stem may have been placed according to a plan as described herein, wherein the pelvis 10 and femur 12 are tracked by the navigation system. Then, the femur 12 may be rotated with respect to the pelvis 10 as described above with respect to Ranawat's sign. By using the navigation system or the like to track the motion of the femur 12 relative to the pelvis 10, the actual combined anteversion can be determined and checked relative to the planned or "target" combined anteversion. Depending on the actual combined anteversion relative to the target combined anteversion, a determination can be made whether or not the plan has been achieved.

Alternatively, the planned or "target" combined anteversion may be derived by applying an arithmetic formula as described by Yoshimine and shown in Equation 1 below (see, e.g., Fumihiro Yoshimine, The Safe-zones for Combined Cup and Neck Anteversions That Fulfill the Essential Range of Motion and Their Optimum Combination in Total Hip Replacements, Journal of Biomechanics 29 (2006), pgs. 1315-1323, the contents of which is hereby incorporated by reference in its entirety), $$\beta_{anat}+0.77*b+\alpha=84.3 \qquad \text{Equation 1}$$

wherein $\beta_{anat}$ is the cup anterior opening (anatomic definition) in degrees, b is the neck anteversion around the vertical axis from the coronal plane in degrees, and $\alpha$ is the cup lateral opening (abduction) in degrees. $\beta_{anat}$ and $\alpha$ characterize the cup position, while b characterizes the neck or stem position.

Each of the above components is related to the other (i.e., changing one parameter affects the other parameters). Using computer analysis, a preferred relationship between the neck anteversion (b) and the cup anteversion ($\alpha$) can be established.

For example, based on a verified neck anteversion (b) and known cup anterior opening ($\beta_{anat}$) as determined, for example, by the navigation system, Equation 1 can provide a cup anteversion ($\alpha$) that is dependent on the neck anteversion (i.e., solving for $\alpha$). Then, using the verified neck anteversion (b) and the derived cup anteversion ($\alpha$), the surgeon can review an implant database (which may be stored in or accessible by the navigation system) relative to a stored neutral, and select an implant that provides the target combined anteversion. The planned positions of the cup and/or stem may be fine tuned with computer assistance so as to develop an overall plan for the placement of the cup and stem that minimizes the likelihood of impingement.

Yet another way of determining the added anteversion may be based on an arithmetic formula as described by Widmer et al. and shown in Equation 2 below (see, e.g., K. H. Widmer, B. Zurfluh, Compliant Positioning of Total Hip Components for Optimal Range of Motion, Journal of Orthopaedic Research 22 (2004), pgs. 815-821, the contents of which is hereby incorporated by reference in its entirety).

$$\text{Cup anteversion}+0.7 \text{ Stem anteversion}=37.3 \qquad \text{Equation 2}$$

Based on a known stem anteversion (e.g., verified by a navigation system), a cup anteversion can be determined. Using these values, the surgeon can review the implant database as described above relative to a stored neutral, and select an implant that provides the target combined anteversion and determine a planned location for the cup and stem.

The method described herein is advantageous for a number of reasons. First, it provides a more consistent and direct way of relating implant positioning for total hip arthoplasty, as it deals primarily with stability through combined anteversion instead of an arbitrary plane of the pelvis. Further, it describes the least variability in intraoperative assessment of both components simultaneously and has a wide range of usage in the medical community.

With respect to conventional "non-navigated" approaches, the method provides additional benefits. For example, the surgeon's visual judgement regarding the position of the calcar of the broach with respect to entering the projected cup position and being centered in the apex is significantly less accurate than computer navigated methods. Similarly, the cup placement from the calcar can be stored in memory of the navigation computer and used throughout the procedure. Thus, continued reassessment is not necessary, thereby minimizing inaccuracies. Further, the degree of internal rotation can be assessed more accurately with navigation tracking of the limb's position. Also, visualization is not necessary to judge Ranawat's sign, which allows for better assessment of decreased visualization via minimally invasive surgery.

Figure 2:
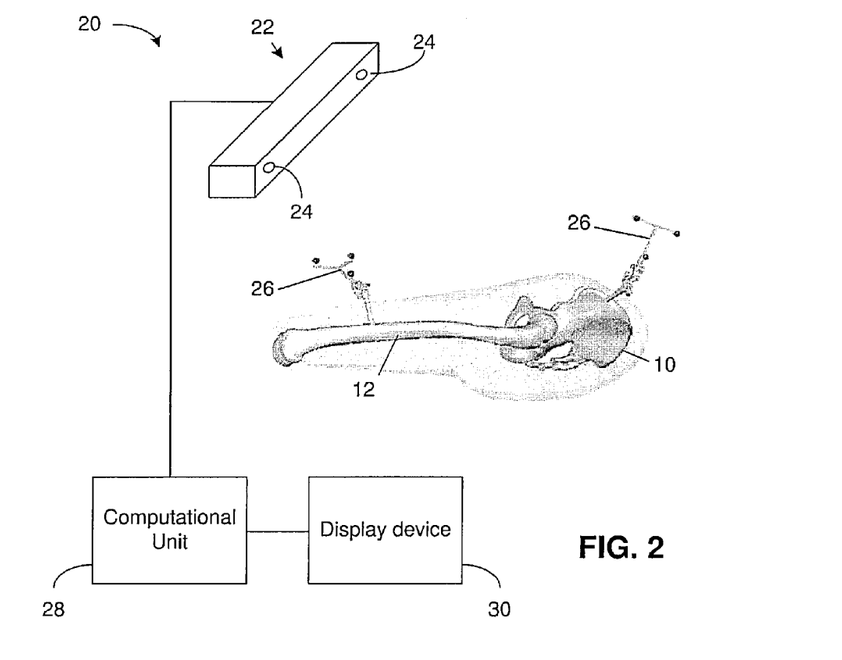
FIG. 2 is a schematic diagram illustrating an exemplary navigation system that may be used to carry out a method in accordance with the invention.

Moving now to FIG. 2, there is shown an exemplary navigation system 20 that may be used in conjunction with and/or to implement the method described herein. The navigation system 20 can include a tracking system 22, wherein the tracking system 22 is operative to localize points in three-dimensional space. The tracking system 22 may be an optical tracking system, for example, wherein the optical tracking system includes two or more cameras 24 that are operative to detect light in the visible and/or infrared spectrum. One or more tracking elements 26, such as a reference star or the like, may be fixed to an object to be tracked, such as the hip 10 and femur 12, for example. The tracking elements 26 are operative to emit or reflect light, and this emitted or reflected light is detectable by the cameras 24 of the tracking system 22. Based on the detected light, the tracking system 22 can localize the tracking elements 26 in three-dimensional space and, thus also can localize the position of the object attached to the tracking element 26.

The tracking system 22 is operatively coupled to a computational unit 28, such that the tracking data obtained by the tracking system 22 may be communicated to the computational unit 28. Further, a display device 30 is operatively coupled to the computational unit 28, such that images, instructions, data, etc. may be provided to the surgeon during planning and/or execution of the procedure.

While the navigation system is shown as including the tracking system 22, it should be appreciated that the tracking system 22 may be separate from the navigation system 20. Further, although an optical tracking system is described herein, non-optical tracking systems also may be utilized without departing from the scope of the invention.

The computational unit 28, using the data received from the tracking system 22, can correlate the received data with previously obtained image data of the patient (e.g., CT image data, x-ray data, etc.), such that instruments (which also may be tracked by the tracking system 22) used in the medical workspace can be provided on the display device 30 in the correct orientation and position relative to the previously obtained image data.

Further, the computational unit 28 can implement the method described herein to assist the surgeon in planning and performing the hip transplant procedure. In this manner, the surgeon may be provided with precise information for positioning the cup and stem so as to minimize the likelihood if impingement of the artificial hip joint.

Figure 3:
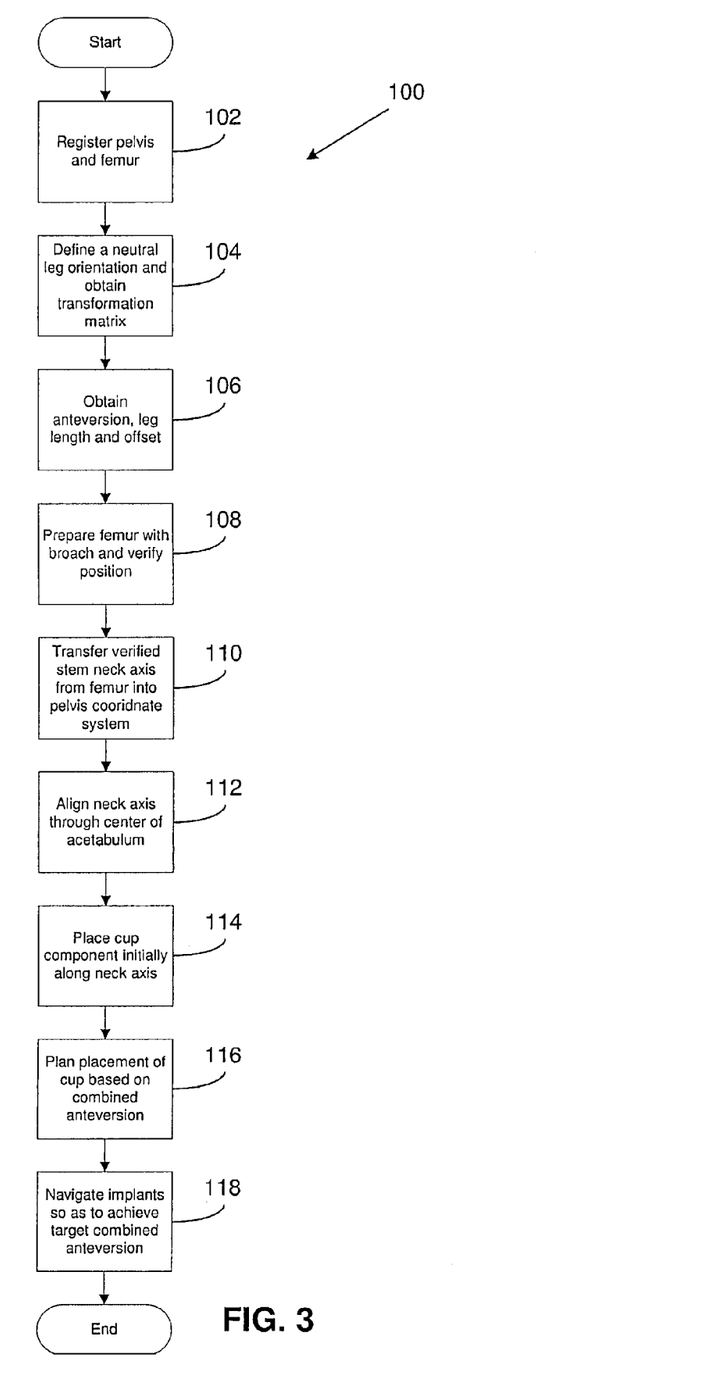
FIG. 3 is a flow diagram illustrating steps of an exemplary method for performing a hip implant based on combined anteversion in accordance with the invention.

Referring now to FIG. 3, a flow diagram 100 illustrating an exemplary method for navigated placement of a pelvic implant based on a previously developed plan is shown. The flow diagram includes a number of process blocks arranged in a particular order. As should be appreciated, many alternatives and equivalents to the illustrated steps may exist and such alternatives and equivalents are intended to fall with the scope of the claims appended hereto. Alternatives may involve carrying out additional steps or actions not specifically recited and/or shown, carrying out steps or actions in a different order from that recited and/or shown, and/or omitting recited and/or shown steps. Alternatives also include carrying out steps or actions concurrently or with partial concurrence.

Beginning at block 102 of FIG. 3, the pelvis 10 and femur 12 of a patient are registered in a medical navigation system 20. For example, and as noted above with respect to FIG. 2, a first trackable element 26 may be fixed to the pelvis 10, and a second trackable element 26 may be fixed to the femur 12, wherein the trackable elements emit or reflect radiation (e.g., infrared or visible light). The emitted or reflected radiation from the respective trackable elements 26 can be detected by the tracking system 22 (e.g., via cameras 24). This information then may be communicated to the computational unit 28 of the navigation system 20 to determine a position of the respective trackable elements in three-dimensional space.

Figure 4A:
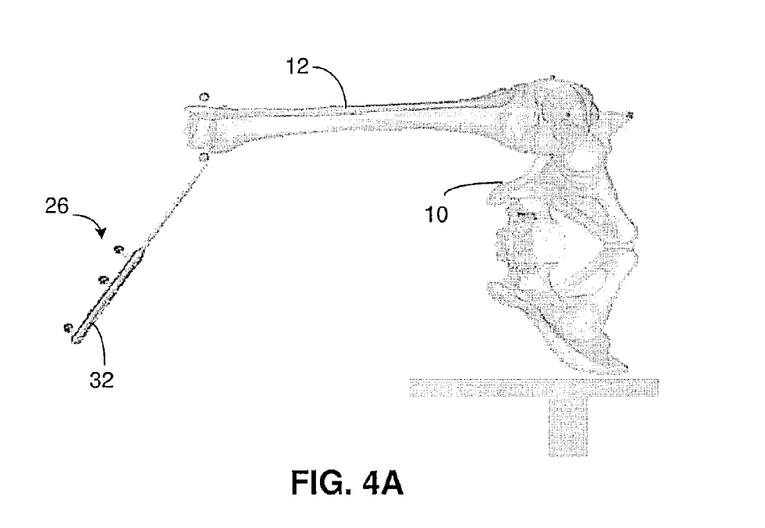
FIGS. 4A-4E are graphical representations of steps of the method of FIG. 3.

With further reference to FIG. 4A, once the trackable elements 26 have been fixed to the pelvis 10 and femur 12, landmarks on the pelvis 10 and femur 12 can be identified to the navigation system 20. The landmarks may be identified, for example, using a pointer 32, wherein the pointer 32 also includes trackable elements 26 such that it also may be localized in three-dimensional space. Based on a known location of the pointer tip (as determined from the trackable elements 26 attached to the pointer 32) the landmarks (and thus their position in three-dimensional space) can be identified and stored in the navigation system 20 relative to the trackable elements 26 of the pelvis 10 and femur 12. Exemplary landmarks may include the anterior superiorilia spine on the side to be treated, the medial and lateral epicondyle, the medial and lateral thalus, the piriformin fossa landmark, and multiple acetabular landmarks.

Further, AKP (ankle center, knee center, piriformis point) may be utilized to register a limb axis of the femur. Using AKP, when ankle points are registered in 90 degrees of flexion, the limb or femoral axis represents the posterior condyles. This is advantageous in that it enables the femoral axis to be referenced to the hip center for calculation of femoral anteversion.

During a portion of the registration process, the leg may be aligned in a neutral position so as to obtain a zero position for the leg, as indicated at block 104. This can be used to calculate a transformation matrix that enables the transfer of information regarding the femur 12 into a pelvic coordinate system. It is preferable that the leg be aligned in the neutral position prior to obtaining the medial and lateral epicondyle, medial and lateral thalus, piriformis fossa and acetabular landmarks.

Figures 4B, 4C:
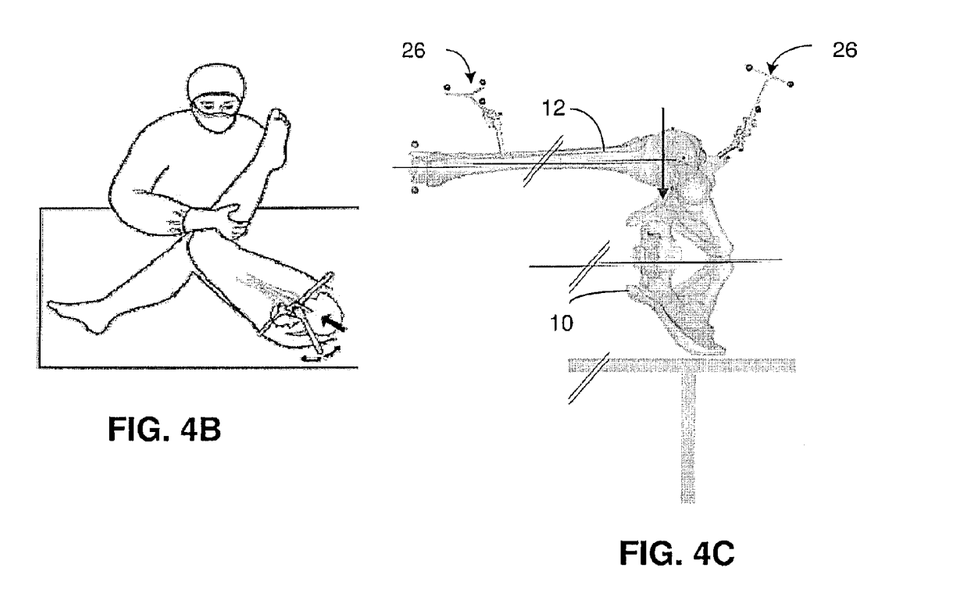

For example, and with reference to FIGS. 4B and 4C, the patient's leg may be placed in a neutral position (e.g., a straight position such as a normal standing position of the femur 12 relative to the pelvis 10). Once in a neutral position, the leg's trajectory may be identified and stored as the zero point for flexion, extension, internal rotation, external rotation, and/or ab/adduction of the femur 12. This data may be recorded and used for the application of Ranawat's sign, for example, as described below. Recordation of the data may be initiated by providing the navigation system 20 with an input signal upon the leg being placed in the neutral position (e.g., via a button or the like that instructs the navigation system to record the data). The neutral leg position also may be used to provide data regarding the extremity for limb length calculations, and the APP can be registered for comparative sake.

Once the landmarks have been identified to the navigation system 20, the pelvis 10 and femur 12 can be registered in the navigation system, i.e, the navigation system 20 can correlate the identified landmarks to previously obtained image data of the patient (e.g., CT image data, x-ray data, etc.). Registration enables the position of instruments within the medical workspace (e.g., within the field of view of the tracking system 22) as well as the orientation of the femur 12 relative to the pelvis 10 to be correctly shown with respect to the previously obtained image data set (e.g., shown on the display device 30).

At block 106, the femur anteversion, leg length and offset can be obtained. This information can be stored for later use to ensure proper alignment and geometry of the implant relative to the hip joint's original geometry.

Figure 4D:
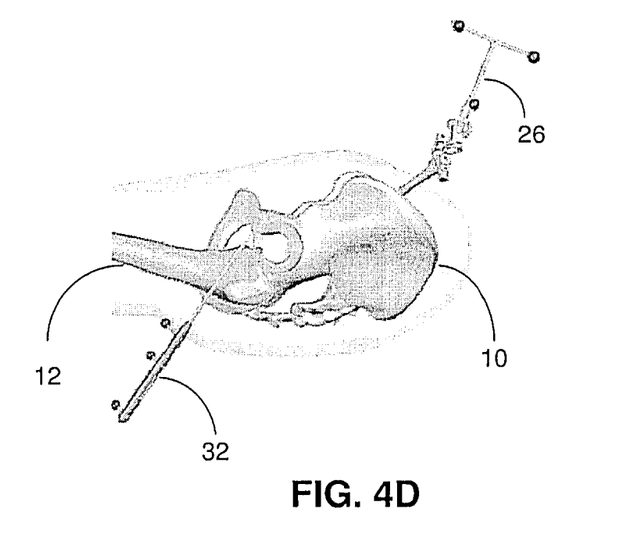
Figure 4E:
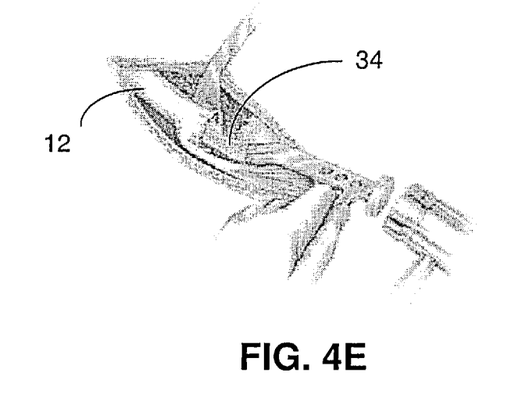

At block 108, the femur 12 is prepared for the implant, and its position in three-dimensional space is verified. Preparation can include, for example, resection of the femoral head. This provides access to the acetabulum, thereby enabling multiple acetabular landmarks to be obtained for additional registration of the pelvis 10, as shown in FIG. 4D. Also, a broach 34 may be used to prepare the femoral canal for the femoral stem, as shown in FIG. 4E. The location of the broach 34 within the femoral canal may be verified using a verification tool, such as the pointer 32, for example. Based on the verified location of the broach 34, the stem axis and angle of the calcar can be registered to the femoral implant.

At block 110, the verified stem neck axis of the femur is transferred to the coordinate system of the pelvis using the transformation matrix derived during registration. With the aid of the navigation system 20, the stem neck axis of the femur 12 is aligned through the center of the acetabulum, as indicated at block 112. Next at block 114, the cup component is initially placed in the pelvis 10 along the neck axis of the femur 12 so as to provide an initial cup location. For example, the computational unit 28, based on the verified calcar position, can position the cup such that the trajectory of the calcar (i.e., the femur neck axis) is centralized at an apex of the cup.

At block 116, a plan is developed based on the principle of combined anteversion for the placement of the cup relative to the verified stem position. As discussed herein, the planned or target combined anteversion may be derived using Ranawat's sign, for example, or via mathematical equations, such as those proposed by Yoshimine, Widmer, etc. Preferably, the planned position of the cup relative to the stem is such that a combined anteversion between a cup component and a stem component is between about 30-45 degrees.

The target combined anteversion of the implant can be planned by referencing the actual patient data collected at block 106 (i.e., the femur anteversion, leg length and offset), and adding an anteversion angle determined using Ranawat's sign. More specifically, the information obtained at block 106 can be used, for example, to determine a mid-sagittal plane of the pelvis (which can be used to calculate the opening or cup inclination), to set the femoral stem so as to provide the proper leg length, as well as neutral values that can be used to calculate an amount of internal rotation already delivered to the joint prior to applying Ranawat's sign or maximizing the component's positions to known range of motions.

Instead of using Ranawat's sign, a target combined anteversion may be planned by using Yoshimine's formula, wherein the anteversion of the femur (b) as derived in block 108 and a known cup anterior opening (βanat) are used in Equation 1 to derive the cup anteversion (α) such that the combined anteversion of the femoral and cup axis is between 30 degrees and 45 degrees, for example.

Then, at block 118, the target combined anteversion as planned in block 116 is used to navigate the cup into position on the pelvis 10 such that the combined anteversion of the cup component and stem component is substantially the same as the target combined anteversion.

In another embodiment of the invention, the cup and femoral stem may be placed on the patient and the stem may be verified as described above. Then, deviations of the combined anteversion may be output on the display device 30 or otherwise provided to the surgeon, who then may evaluate the recommendations and act accordingly.

Accordingly, the above described methods enable the femoral stem to be placed prior to the cup. Then, based on combined anteversion, the cup can be placed so as achieve an optimal geometry that minimizes the likelihood of impingement. Moreover, the location of the cup and stem may be planned prior to actual trial fitment.

While the above methods have been described with respect to a "stem first" approach, they also may be applicable in a "cup first" approach. This is particularly true when femoral stems that incorporate particular adjustments are used (e.g., rotation or angular adjustments of the stem relative to the head and/or neck). For example, the cup may be placed in a certain position, and then the stem may be adjusted to provide the target combined anteversion.

Using a cup first approach with a modular femoral stem, the cup may be first attached to the pelvis 10. Then, combined anteversion as described herein can be planned and applied, wherein an anteversion angle of the stem component may be made dependent on the anteversion angle of the cup component (e.g., instead of solving for α, Equation 1 is solved for b). The combined anteversion can be achieved by adjusting the femoral stem so as to achieve the target combined anteversion.

Accordingly, the combined anteversion may be dialed in via the stem, as opposed to the cup.

Figure 5:
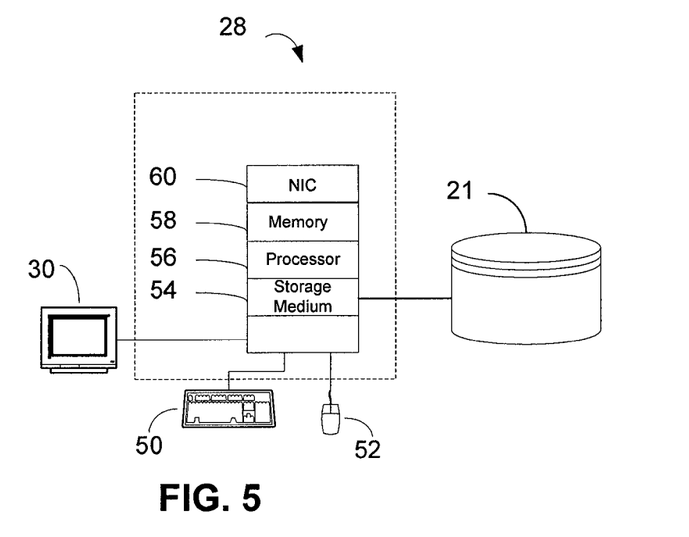
FIG. 5 is a block diagram of an exemplary computational unit that may be used in the navigation system of FIG. 2.

Moving now to FIG. 5 there is shown a block diagram of an exemplary computational unit 28 that may be used to implement one or more of the methods described herein. The computational unit 28 may include a display device 30 for viewing system information, and a keyboard 50 and pointing device 52 for data entry, screen navigation, etc. A computer mouse or other device that points to or otherwise identifies a location, action, etc., e.g., by a point and click method or some other method, are examples of a pointing device 52. Alternatively, a touch screen (not shown) may be used in place of the keyboard 50 and pointing device 52. The display device 30, keyboard 50 and pointing device 52 communicate with a processor via an input/output device 54, such as a video card and/or serial port (e.g., a USB port or the like).

A processor 56, such as an AMD Athlon 64® processor or an Intel Pentium IV® processor, combined with a memory 58 execute programs to perform various functions, such as data entry, numerical calculations, screen display, system setup, etc. The memory 58 may comprise several devices, including volatile and non-volatile memory components. Accordingly, the memory 58 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 56 and the memory 58 are coupled using a local interface (not shown). The local interface may be, for example, a data bus with accompanying control bus, a network, or other subsystem.

The memory may form part of a storage medium for storing information, such as application data, screen information, programs, etc., part of which may be in the form of a database. The storage medium may be a hard drive, for example, or any other storage means that can retain data, including other magnetic and/or optical storage devices. A network interface card (NIC) 60 allows the computational unit 28 to communicate with other devices.

A person having ordinary skill in the art of computer programming and applications of programming for computer systems would be able in view of the description provided herein to program a computer system 30 to operate and to carry out the functions described herein. Accordingly, details as to the specific programming code have been omitted for the sake of brevity. Also, while software in the memory 58 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for placing a pelvic implant in a patient, said pelvic implant including a cup having a predetermined cup component and a femoral stem having a predetermined stem component, comprising:
    obtaining image data corresponding to the cup and femoral stem;
    using the image data to display a geometrical relationship between the cup and the femoral stem corresponding to a location of the cup and femoral stem in the patient;
    determining a target combined anteversion for relative orientation of the cup component and the stem component; and
    virtually positioning at least one of the cup within the patient's pelvis or the stem within the patient's femur such that a combined anteversion between the predetermined cup component and the predetermined femoral stem component corresponds to the target combined anteversion, wherein virtually positioning includes determining a geometry of the femoral stem after the cup has been placed in the pelvis.

2. The method according to claim 1, further comprising navigating the cup or femoral stem into position in the patient based on the location of the cup or femoral stem that corresponds to the target combined anteversion.

3. The method according to claim 1, wherein the cup component is an axis central to an apex of the cup, and the femoral stem component is an axis on a longitudinal centerline of a neck of the femoral stem.

4. The method according to claim 1, further comprising:
    registering the patient's pelvis and femur in a medical workspace;
    obtaining from the registered pelvis and femur a transformation matrix for transferring information regarding the femur to a pelvic coordinate system;
    using the transformation matrix to transfer a neck axis to the pelvic coordinate system;
    aligning the neck axis through a center of an acetabulum of the pelvis; and
    placing the cup component along the neck axis.

5. The method according to claim 4, wherein registering includes:
    placing a leg corresponding to the patient's femur in a neutral orientation;
    determining a trajectory of the femur while the leg is in the neutral position; and
    storing the trajectory as a zero point for flexion, extension internal rotation, external rotation, abduction or adduction of the femur.

6. The method according to claim 1, wherein virtually positioning includes using the formula $\beta_{anat}+0.77*b+\alpha=84.3$ to determine an anteversion of the cup component and/or the femoral stem component.

7. The method according to claim 1, further comprising adjusting geometric features of the stem so as to achieve the target combined anteversion.

8. The method according to claim 1, wherein virtually positioning includes determining a location of the cup after virtually placing the femoral stem in the femur.

9. The method according to claim 1, wherein virtually positioning at least one of the location of the cup within the pelvis and the location of the stem within the femur includes identifying a cup axis of the cup and a neck axis of the femoral stem, and placing an anteversion of the cup axis dependent on an anteversion of the neck axis, or placing an anteversion of the neck axis dependent on an anteversion of the cup axis.

10. The method according to claim 9, further comprising placing the cup component neutral with respect to the femoral stem component.

11. The method according to claim 10, wherein placing the cup component neutral includes adding anteversion to the cup component.

12. The method according to claim 1, wherein the target combined anteversion is between 30 degrees and 45 degrees.

13. The method according to claim 1, wherein virtually positioning includes:
   predicting a location of an impingement of the pelvic implant; and
   selecting a cup placement relative to the predicted impingement locations so as to minimize the occurrence of the impingement.

14. The method according to claim 1, wherein virtually positioning includes using Ranawat's sign to the planned placement of the cup and the femoral stem to determine an anteversion to be added to a cup axis of the cup or a neck axis of the femoral stem so as to achieve the target combined anteversion.

* * * * *